(12) United States Patent
Matsubara et al.

(10) Patent No.: US 10,159,813 B2
(45) Date of Patent: Dec. 25, 2018

(54) GAS SUPPLY MASK APPARATUS

(71) Applicant: Atom Medical Corporation, Tokyo (JP)

(72) Inventors: Kazuo Matsubara, Tokyo (JP); Terumi Matsubara, Saitama (JP); Kenji Kobayashi, Saitama (JP); Shinichi Kobayashi, Saitama (JP)

(73) Assignee: Atom Medical Corporation, Tokyo (JP)

( * ) Notice: Subject to any disclaimer, the term of this patent is extended or adjusted under 35 U.S.C. 154(b) by 625 days.

(21) Appl. No.: 14/717,173

(22) Filed: May 20, 2015

(65) Prior Publication Data

US 2015/0335847 A1    Nov. 26, 2015

(30) Foreign Application Priority Data

May 21, 2014  (JP) .................................. 2014-105147
May 30, 2014  (JP) .................................. 2014-112844
Jun. 12, 2014  (JP) .................................. 2014-121585

(51) Int. Cl.
*A61M 16/06*     (2006.01)
*A61M 16/08*     (2006.01)

(52) U.S. Cl.
CPC ........ *A61M 16/0683* (2013.01); *A61M 16/06* (2013.01); *A61M 16/0816* (2013.01); *A61M 2202/0208* (2013.01)

(58) Field of Classification Search
CPC .......... A61M 16/0683; A61M 16/0688; A61M 16/0694; A61M 2202/0208; A62B 18/00; A62B 18/003; A62B 18/006; A62B 18/02; A62B 18/025; A62B 18/04; A62B 18/045; A62B 18/06; A62B 18/08; A62B 18/082; A62B 18/084; A62B 18/086;
(Continued)

(56) References Cited

U.S. PATENT DOCUMENTS 2,248,477 A * 7/1941 Lombard .......... A61M 16/0683
                                              128/205.25
2,535,938 A   12/1950 Lombard
(Continued)

FOREIGN PATENT DOCUMENTS

JP    S34-9100 B    10/1959
JP    S6318154 U    2/1988
(Continued)

OTHER PUBLICATIONS

Office Action issued in JP Application No. 2014-105147 dated Apr. 20, 2017.
(Continued)

*Primary Examiner* — Joshua Lee
(74) *Attorney, Agent, or Firm* — Hunton Andrews Kurth LLP

(57) ABSTRACT

A gas supply mask apparatus comprises a mask main body which can be put on a mask wearer relatively simply and relatively reliably by extending a head-worn band such as an elastic bandage relatively simply and relatively reliably over the head of the mask wearer even when there is no head-worn string such as a rubber string at hand. A string attaching short hole and band attaching long hole are formed in each of the left and right end portions of the outer peripheral portion of the mask main body.

23 Claims, 6 Drawing Sheets

(58) Field of Classification Search
CPC . A62B 18/088; A62B 18/10; B63C 2011/128; A41D 13/1161; A63B 71/10; A61F 9/027; A42B 7/00
See application file for complete search history.

(56) References Cited

U.S. PATENT DOCUMENTS

| | | | |
|---|---|---|---|
| 2,928,387 A | 3/1960 | Layne | |
| 3,042,035 A | 7/1962 | George | |
| 3,680,555 A | 8/1972 | Warncke | |
| 3,850,171 A * | 11/1974 | Ball | A61M 16/06 128/204.25 |
| 4,201,205 A | 5/1980 | Bartholomew | |
| 4,279,037 A * | 7/1981 | Morgan | A42B 3/08 2/421 |
| 4,794,921 A | 1/1989 | Lindkvist | |
| 4,875,477 A * | 10/1989 | Waschke | A61B 5/02438 128/206.21 |
| 5,005,571 A * | 4/1991 | Dietz | A61M 16/06 128/205.25 |
| 5,441,046 A * | 8/1995 | Starr | A61M 16/0683 128/206.27 |
| 5,465,712 A | 11/1995 | Malis et al. | |
| 5,483,953 A | 1/1996 | Cooper | |
| 5,724,965 A * | 3/1998 | Handke | A61M 16/06 128/205.25 |
| 5,738,094 A | 4/1998 | Hoftman | |
| 6,035,852 A | 3/2000 | Hoftman | |
| 6,491,034 B1 | 12/2002 | Gunaratnam et al. | |
| 6,675,796 B2 | 1/2004 | McDonald | |
| 7,926,487 B2 * | 4/2011 | Drew | A61M 16/06 128/204.18 |
| 8,042,540 B2 | 10/2011 | McDonald | |
| 8,646,449 B2 | 2/2014 | Bowsher | |
| 8,733,356 B1 * | 5/2014 | Roth | A62B 18/08 128/205.27 |
| 9,010,330 B2 * | 4/2015 | Barlow | A61M 16/06 128/205.25 |
| 9,144,656 B2 * | 9/2015 | Lang | A61M 16/06 |
| 9,186,474 B1 | 11/2015 | Rollins | |
| 9,272,108 B2 | 3/2016 | Hu | |
| 2003/0154984 A1 * | 8/2003 | Fernandes | A41D 13/1146 D24/110.1 |
| 2004/0045550 A1 * | 3/2004 | Lang | A61M 16/06 128/205.25 |
| 2004/0112385 A1 | 6/2004 | Drew et al. | |
| 2006/0048774 A1 | 3/2006 | Townsend | |
| 2006/0081248 A1 * | 4/2006 | McDonald | A61M 16/06 128/205.25 |
| 2006/0102185 A1 | 5/2006 | Drew et al. | |
| 2006/0196510 A1 * | 9/2006 | McDonald | A61M 16/06 128/206.21 |
| 2007/0125379 A1 | 6/2007 | Pierro et al. | |
| 2008/0149105 A1 * | 6/2008 | Matula | A61M 16/06 128/206.29 |
| 2009/0050156 A1 | 2/2009 | Ng et al. | |
| 2009/0250061 A1 | 10/2009 | Marasigan | |
| 2009/0260628 A1 | 10/2009 | Flynn | |
| 2010/0122705 A1 | 5/2010 | Moenning | |
| 2010/0236549 A1 | 9/2010 | Selvarajan et al. | |
| 2010/0258133 A1 | 10/2010 | Todd et al. | |
| 2011/0155140 A1 * | 6/2011 | Ho | A61M 16/0488 128/207.18 |
| 2011/0180078 A1 * | 7/2011 | McKinley | A41D 13/1161 128/863 |
| 2011/0197341 A1 * | 8/2011 | Formica | A61M 16/0683 2/209.3 |
| 2012/0042878 A1 * | 2/2012 | Woo | A62B 18/025 128/206.15 |
| 2012/0055485 A1 * | 3/2012 | Anthony | A61M 16/06 128/207.18 |
| 2012/0204872 A1 | 8/2012 | Cohen et al. | |
| 2012/0222678 A1 * | 9/2012 | Colbaugh | A61M 16/0666 128/205.25 |
| 2012/0318271 A1 * | 12/2012 | Ho | A61M 16/0666 128/205.25 |
| 2012/0318274 A1 * | 12/2012 | Ho | A61M 16/0666 128/207.18 |
| 2013/0192601 A1 | 8/2013 | Reischl et al. | |
| 2014/0090649 A1 * | 4/2014 | Groll | A61M 16/06 128/205.25 |
| 2014/0107517 A1 * | 4/2014 | Hussain | A61M 16/0672 600/532 |
| 2014/0150798 A1 | 6/2014 | Fong et al. | |
| 2014/0305433 A1 | 10/2014 | Rothermel | |
| 2014/0305436 A1 | 10/2014 | Nitta | |
| 2015/0107586 A1 | 4/2015 | Kuo | |
| 2015/0297854 A1 | 10/2015 | McCracken | |
| 2015/0328423 A1 | 11/2015 | Slew et al. | |
| 2016/0008558 A1 | 1/2016 | Huddart et al. | |
| 2016/0184549 A1 | 6/2016 | Bugamelli et al. | |
| 2016/0310688 A1 | 10/2016 | Rothermel | |

FOREIGN PATENT DOCUMENTS

| | | |
|---|---|---|
| JP | 2005-253925 | 9/2005 |
| WO | 2013144753 A1 | 10/2013 |

OTHER PUBLICATIONS

Office Action issued in JP Application No. 2014-121585 dated May 10, 2017.
Office Action issued in JP Application No. 2014-112844 dated May 12, 2017.
Non-final Office Action dated Sep. 23, 2017, in U.S. Appl. No. 14/717,163.
Non-final Office Action dated Sep. 23, 2017, in U.S. Appl. No. 14/717,180.

* cited by examiner

GAS SUPPLY MASK APPARATUS

CROSS-REFERENCE TO RELATED PATENT APPLICATIONS

This patent application claims priority to Japan Patent Application No. 2014-105147, filed May 21, 2014, and Japan Patent Application No. 2014-112844, filed May 30, 2014, and Japan Patent Application No. 2014-121585, filed Jun. 12, 2014, the disclosures of each of which are herein incorporated by reference in their entirety.

TECHNICAL FIELD

The present invention relates to a gas supply mask apparatus such as an oxygen mask apparatus comprising a mask main body wearable on the head of a mask wearer, and configured to introduce a gas into a gas introduction space existing between the mask main body put on the head and a face of the mask wearer.

BACKGROUND OF THE INVENTION

An oxygen mask apparatus is disclosed in Japanese Patent Laid-Open No. 2005-253925 (to be referred to as "the above-mentioned prior patent literature" hereinafter). In this oxygen mask apparatus disclosed in the above-mentioned prior patent literature, a plurality of rubber string attaching round holes are formed in the left and right end portions of the outer peripheral portion of the mask main body. Therefore, the mask wearer can attach the two end portions of a rubber string to the rubber string attaching round hole in the left end portion and the rubber string attaching round hole in the right end portion of the outer peripheral portion of the mask main body. Accordingly, the mask wearer can wear the oxygen mask apparatus by extending the rubber string over his or her head.

Unfortunately, when using the oxygen mask apparatus disclosed in the above-mentioned prior patent literature, if the mask wearer has no rubber string at hand, he or she must acquire a rubber string by some method. If it takes much labor or a long time to acquire a rubber string, the mask wearer requires an extra labor or extra time before he or she can begin using the oxygen mask apparatus.

SUMMARY OF THE INVENTION

The present invention can effectively correct the above-described drawback of the conventional oxygen mask apparatus disclosed in the above-mentioned related-art patent literature by using a novel arrangement.

The present invention is directed to a gas supply mask apparatus comprising a mask main body wearable on a head of a mask wearer, and configured to introduce a gas into a gas introduction space existing between the mask main body put on the head and a face of the mask wearer, wherein a string attaching short hole and a band attaching long hole are formed in each of a left end portion and a right end portion of an outer peripheral portion of the mask main body. In this arrangement, the string attaching short hole and band attaching long hole are formed in each of the left and right end portions of the outer peripheral portion of the mask main body. Therefore, when the mask wearer has a head-worn string such as a rubber string at hand, the mask wearer can relatively simply and relatively reliably wear the mask main body by simply and reliably extending the head-worn string over the head or the like of the mask wearer. When the mask wearer has no head-worn string such as a rubber string at hand, the mask wearer can simply and reliably wear the mask main body by extending a head-worn band such as an elastic bandage over the head or the like of the mask wearer. Note that this feature applies even when the mask wearer has a head-worn string such as a rubber string at hand.

According to the first aspect, the present invention preferably has an arrangement in which each of the left and right end portions of the outer peripheral portion is formed into a substantially flat surface. In this arrangement, it is possible to attach a head-worn elastic string, such as a rubber string or a head-worn elastic band or elastic bandage, to the left and right end portions of the outer peripheral portion of the mask main body.

According to the second aspect, the present invention preferably has an arrangement in which a left hole formation projection and a right hole formation projection are formed in substantially middle portions of the left end portion and the right end portion of the outer peripheral portion, such that the left hole formation projection and the right hole formation projection project substantially outward to the left and right, one of the string attaching short hole and the band attaching long hole is formed in each of the left hole formation projection and the right hole formation projection, and the other of the string attaching short hole and the band attaching long hole is formed in each of the left end portion and the right end portion of the outer peripheral portion, such that the other of the string attaching short hole and the band attaching long hole is adjacent to each of the left hole formation projection and the right hole formation projection. In this arrangement, standard-height attaching portions of the left and right end portions of the mask main body can be indicated by the left and right hole formation projections. Accordingly, the mask wearer or the like can further simply and further reliably wear the mask main body on his or her head.

According to the first mode of the second aspect, the present invention preferably has an arrangement in which the string attaching short hole is formed in each of the left hole formation projection and the right hole formation projection, and the band attaching long hole is formed in each of the left end portion and the right end portion of the outer peripheral portion, such that the band attaching long hole is adjacent to each of the left hole formation projection and the right hole formation projection. In this arrangement, the above-described effect of the second aspect can be achieved better with almost no decrease in strength of the pair of left and right hole formation projections.

According to the second mode of the second aspect, the present invention preferably has an arrangement in which the left hole formation projection and the right hole formation projection are respectively integrated with and substantially flush with the left end portion and the right end portion. According to the third mode of the second aspect, the present invention preferably has an arrangement in which each of the left hole formation projection and the right hole formation projection is formed into one of a substantially trapezoidal shape, a substantially rectangular shape, a substantially semi-circular shape, a substantially semi-elliptical shape, and a substantially semi-oval shape. In this case (in other words, according to a preferred form of the third mode of the second aspect), each of the left hole formation projection and the right hole formation projection is more preferably formed into a substantially isosceles trapezoidal shape which projects to narrow substantially outward to left or right. The above-described effect achieved by the second aspect can be achieved better by one, two, or all of these three types of arrangements (in other words, the arrangement of the second mode of the second aspect, the arrangement of the third mode of the second aspect, and the arrangement of the preferred form of the third mode of the second aspect).

According to a practical example of the preferred form of the third mode of the second aspect, the present invention preferably has an arrangement in which a length of a base of each of the left hole formation projection and the right hole formation projection falls within a range of 10.5 to 17.5 mm (more preferably, a range of 11.2 to 16.8 mm, and most preferably, a range of 11.7 to 16.3 mm), a projection height of each of the left hole formation projection and the right hole formation projection falls within a range of 4.5 to 7.5 mm (more preferably, a range of 4.8 to 7.2 mm, and most preferably, a range of 5.0 to 7.0 mm), and an area of each of the left hole formation projection and the right hole formation projection falls within a range of 45 to 75 $mm^2$ (more preferably, a range of 48 to 72 $mm^2$, and most preferably, 50 to 70 $mm^2$). Furthermore, according to the fourth mode of the second aspect, the present invention preferably has an arrangement in which a ratio of a length in a vertical direction from an upper end of the mask main body to a substantially center of each of the pair of left and right hole formation projections to a length in the vertical direction of the mask main body falls within a range of 0.38 to 0.48 (more preferably, a range of 0.39 to 0.47, and most preferably, a range of 0.40 to 0.46). The above-described effect achieved by the second aspect can be achieved better by one or both of these two types of arrangements (in other words, the arrangement of the practical example of the preferred form of the third mode of the second aspect and the arrangement of the fourth mode of the second aspect).

According to the third aspect, the present invention preferably has an arrangement in which a maximum length of each of the string attaching short holes in a planar view falls within a range of 1.5 to 2.5 mm (more preferably, a range of 1.6 to 2.4 mm, and most preferably, a range of 1.7 to 2.3 mm), and an area of each of the string attaching short holes in a planar view falls within a range of 2.35 to 3.95 $mm^2$ (more preferably, a range of 2.50 to 3.80 $mm^2$, and most preferably, a range of 2.62 to 3.66 $mm^2$). According to the fourth aspect, the present invention preferably has an arrangement in which a width of each of the band attaching long holes in a planar view falls within a range of 0.75 to 1.25 mm (more preferably, a range of 0.80 to 1.20 mm, and most preferably, a range of 0.82 to 1.18 mm), a maximum length of each of the band attaching long holes in a planar view falls within a range of 7.5 to 12.5 mm (more preferably, a range of 8.0 to 12.0 mm, and most preferably, a range of 8.2 to 11.8 mm), and an area of each of the band attaching long holes in a planar view falls within a range of 6.8 to 11.4 $mm^2$ (more preferably, a range of 7.2 to 10.8 $mm^2$, and most preferably, a range of 7.5 to 10.5 $mm^2$). The above-described effects achieved by the second and third aspects can be achieved better by one or both of these two types of arrangements (in other words, the arrangement of the third aspect and the arrangement of the fourth aspect).

The above and other objects, features and advantages of this invention will become readily apparent from the following detailed description thereof which is to be read in connection with the accompanying drawings.

DETAILED DESCRIPTION OF THE INVENTION

Next, an oxygen mask apparatus 1 according to an embodiment of the present invention will be explained with reference to FIGS. 1 to 7 by dividing the explanation into "1. Explanation of Oxygen Mask Main Body", "2. Explanation of First to Fourth Connectors and Gas Supply Tube", and "3. Explanation of Operation of Putting Oxygen Mask Apparatus on Mask Wearer".

1. Explanation of Oxygen Mask Main Body

Figure 1:
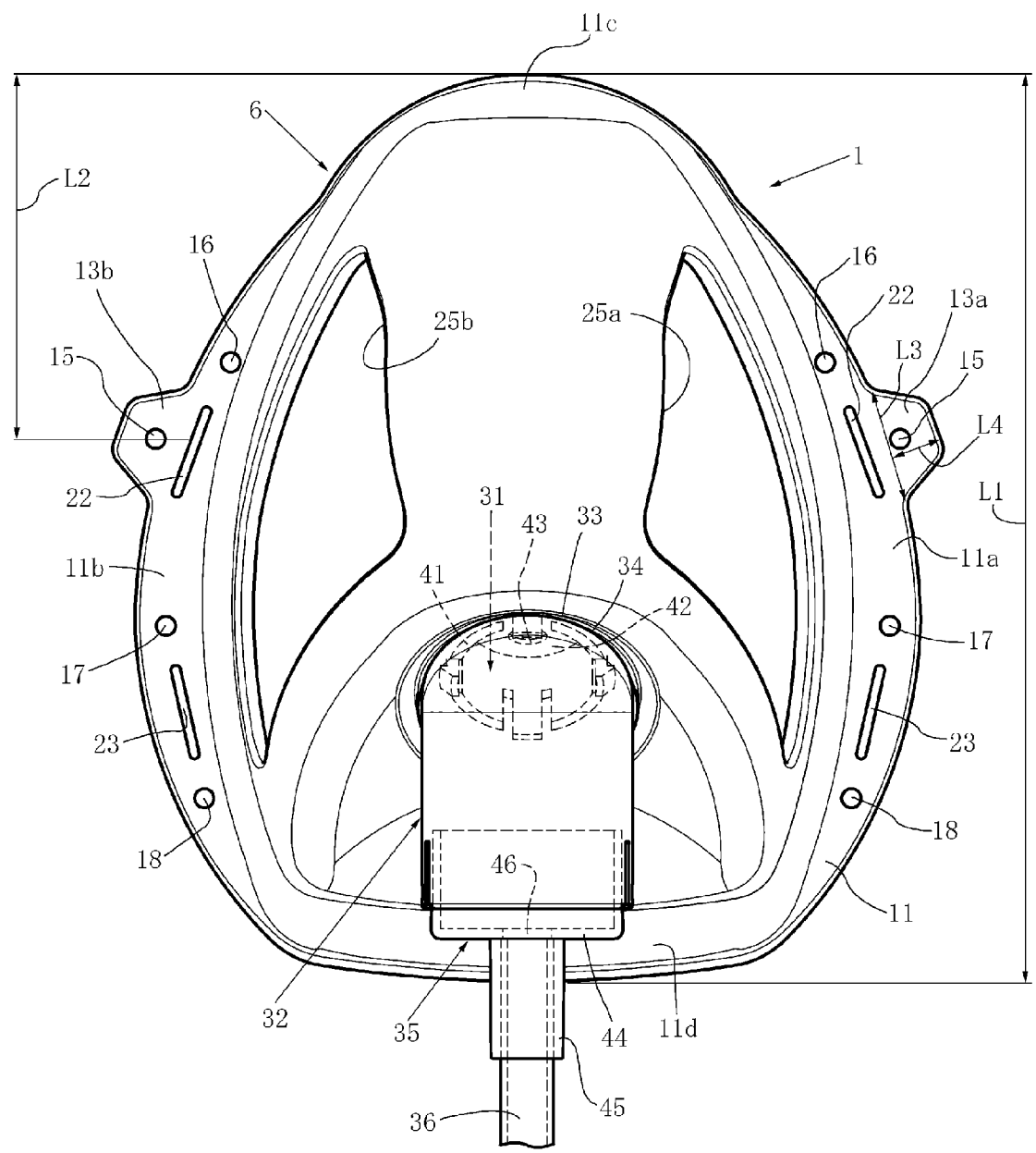
FIG. 1 is a front view of an oxygen mask apparatus according to an embodiment in which the present invention is applied to the oxygen mask apparatus.
Figure 2:
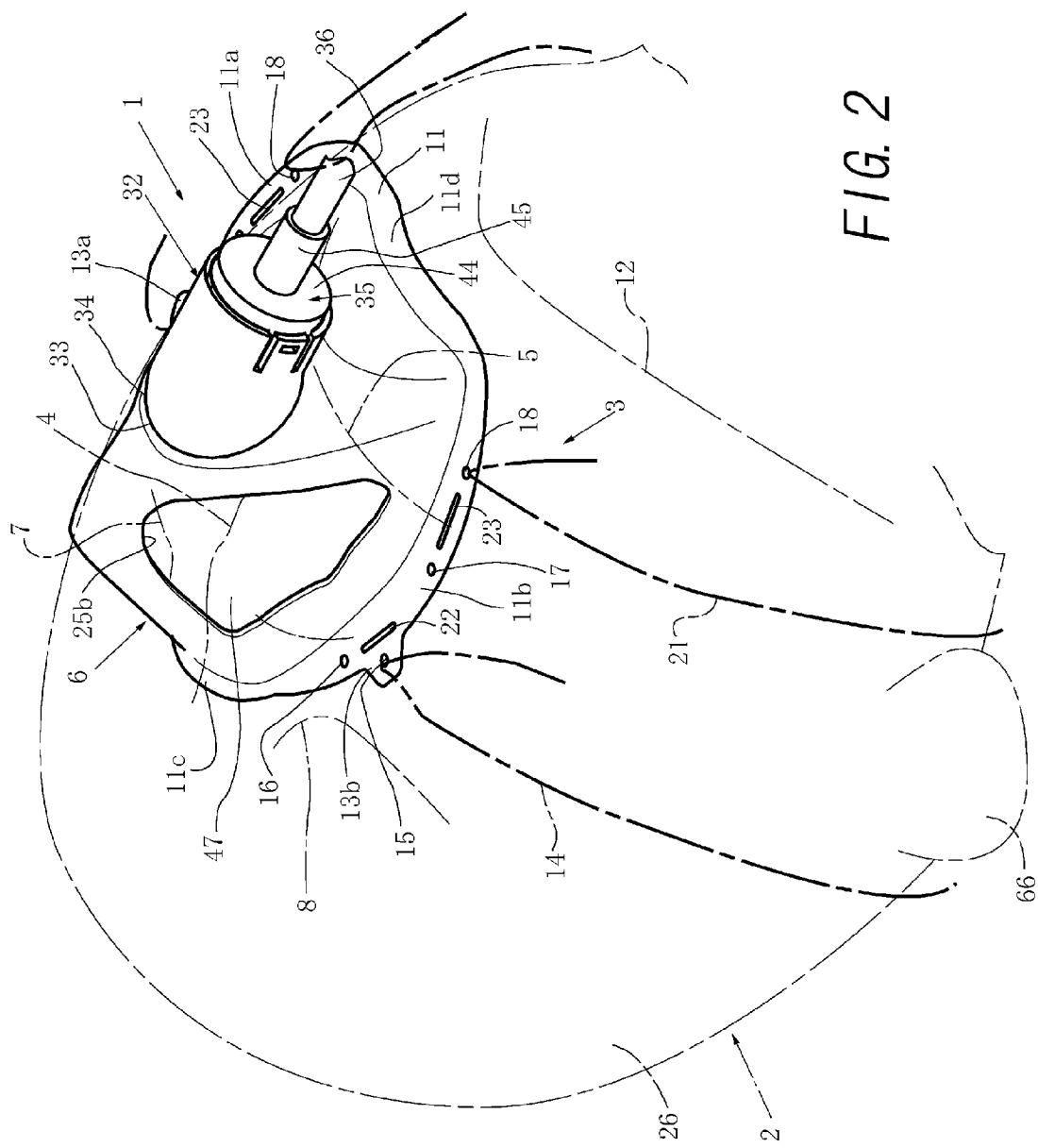
FIG. 2 is a perspective view in a first wearing state of the oxygen mask apparatus shown in FIG. 1.

As shown in FIGS. 1 and 2, the oxygen mask apparatus 1 as a gas supply mask apparatus includes a mask main body 6 capable of covering a substantially central portion (more specifically, a nose 4 and a mouth 5 and their peripheries) of a face 3 of a mask wearer 2 such as a patient. Note that the mask main body 6 can integrally be molded from a substantially transparent (in other words, light-transmitting) soft synthetic resin such as soft vinyl chloride so as to have a substantially bisymmetrical shape and substantially bisymmetrical pattern. Also, in FIG. 2, reference numeral 7 denotes the left eye of the mask wearer 2, and reference numeral 8 denotes the right eye of the mask wearer. At least left and right end portions 11a and 11b of an outer peripheral portion 11 of the mask main body 6 are so formed as to form a substantially flat surface over a substantially whole region. Note that an upper end portion 11c of the outer peripheral portion 11 has a curved shape which substantially continues to the left and right end portions 11a and 11b and slightly projects forward (in other words, outward), so as to substantially fit the shape of the nose 4 of the mask wearer 2. A lower end portion 11d of the outer peripheral portion 11 forms a substantially flat surface which substantially continues to the left and right end portions 11a and 11b, so as to substantially fit a portion (and the vicinity) above a chin 12 of the mask wearer 2. However, the lower end portion 11d may also have a curved shape which substantially continues to the left and right end portions 11a and 11b and slightly projects forward (in other words, outward), so as to substantially fit a lower portion (and the vicinity) of the chin 12 of the mask wearer 2.

As shown in FIGS. 1 and 2, in slightly upper portions of middle portions of the pair of left and right end portions 11a and 11b of the outer peripheral portion 11 of the mask main body 6, each of left and right hole formation projections 13a and 13b is integrated with and substantially flush with a corresponding one of the pair of left and right end portions 11a and 11b. The left and right hole formation projections 13a and 13b project outward from the pair of left and right end portions 11a and 11b to the left and right (preferably, so as to project to narrow outward to the left and right) into a substantially trapezoidal shape such as a substantially isosceles trapezoidal shape, a substantially rectangular shape, a substantially semi-circular shape, a substantially semi-elliptical shape, a substantially semi-oval shape, or the like shape. Also, in each of the left and right hole formation projections 13a and 13b each having a substantially isosceles trapezoidal shape in the embodiment shown in the drawings, a corresponding one of left and right string attaching short holes (in other words, holes which look short in a planar view) 15 is formed as a through hole. The left and right end portions of a first head-worn elastic string having a flat shape (in other words, a flat and relatively narrow elastic member) 14 as a first head-worn longitudinal member having flexibility, elasticity and extensibility can be inserted into and attached to the pair of left and right string attaching short holes 15. In addition, a plurality of, e.g., three similar string attaching short holes (in other words, holes which look short in a planar view) 16, 17, and 18 are sequentially formed as through holes from the upper portion to the lower portion along a substantially vertical direction of each of the pair of left and right end portions 11a and 11b. Furthermore, each of the two end portions of a second head-worn rubber string (in other words, a flat and relatively narrow elastic member) 21 as a second head-worn string which can be formed like the first head-worn rubber string 14 may also be inserted into and attached to one of the three string attaching short holes 16, 17, and 18, instead of or in addition to the first head-worn rubber string 14.

As shown in FIGS. 1 and 2, in each pair of left and right end portions 11a and 11b, a pair of upper and lower bandage attaching long holes (in other words, holes which look narrow in a planar view) 22 and 23 extending substantially linearly along a corresponding one of the pair of left and right end portions 11a and 11b are formed as through holes. Also, the upper bandage attaching long hole 22 of the pair of upper and lower bandage attaching long holes 22 and 23 is adjacent to a corresponding one of the pair of left and right string attaching short holes 15 so as to oppose the corresponding one of the pair of left and right string attaching short holes 15 (in other words, the projection 13a or 13b) in substantially right and left directions (in other words, a crosswise direction). Note that the two end portions of a head-worn elastic bandage (in other words, a flat, extensible and relatively wide elastic member) 24 as a flexible second head-worn longitudinal member can be inserted into and attached to, instead of the first head-worn rubber string 14, the pair of left and right bandage attaching long holes 22 of the bandage attaching long holes 22 and 23. Furthermore, the two end portions of a second head-worn elastic bandage (not shown) as a second longitudinal wearing member may also be inserted into and attached to the pair of left and right bandage attaching long holes 23, instead of or in addition to the head-worn elastic bandage 24. Note that each of the first and second head-worn rubber strings 14 and 21 and the head-worn elastic bandage 24 and above-mentioned second head-worn elastic bandage (in other words, flat and relatively wide first and second elastic members) can be extended over a head (in other words, a head including the face of the mask wearer 2 such as a person) 26 of the mask wearer 2, so as to pass through the left cheek, the back of the head, and the right cheek of the mask wearer 2. Furthermore, at least one of the first head-worn rubber strings (in other words, the elastic members) 14 and 21, and at least one of the head-worn elastic bandage 24 and above-mentioned second head-worn elastic bandage (in other words, the first and second elastic bands such as the first and second elastic bandages) may also be attached to the pair of left and right end portions 11a and 11b and extended over the head 26 of the mask wearer 2 at the same time.

A length L1 in the vertical direction of the mask main body 6 shown in FIG. 1 is substantially 105 mm. A length L2 in the vertical direction from the substantially upper end of the mask main body 6 to a substantially center of the pair of left and right hold formation projections 13a and 13b (in other words, the pair of left and right string attaching short holes 15) is substantially 38 mm. Therefore, a ratio L2/L1 of the length L2 in the vertical direction to a substantially center of the pair of left and right hole formation projections 13a and 13b (in other words, the pair of left and right string attaching short holes 15) to the length L1 in the vertical direction of the mask main body 6 is substantially 0.36. Also, as shown in FIG. 1, a length of the upper base, a length L3 of the lower base and a projection height L4 of the outer side surface and inner side surface of the pair of left and right hole formation projections 13a and 13b each having a substantially isosceles trapezoidal shape or the like shape are respectively substantially 6 mm, substantially 14 mm, and substantially 6 mm. In addition, the area of each of the outer side surface and inner side surface of the pair of left and right hole formation projections 13a and 13b is substantially 60 $mm^2$ To achieve the object of the present invention, the ratio L2/L1 generally preferably falls within the range of 0.38 to 0.48, more preferably, the range of 0.39 to 0.47, and most preferably, the range of 0.40 to 0.46, from the viewpoint of practicality. Also, to achieve the object of the present invention, the length L3 of the lower base as the proximal end or base of each of the outer side surface and inner side surface (in other words, a substantially isosceles trapezoidal shape) of the pair of left and right hole formation projections 13a and 13b generally preferably falls within the range of 10.5 to 17.5 mm, more preferably, the range of 11.2 to 16.8 mm, and most preferably, the range of 11.7 to 16.3 mm, from the viewpoint of practicality. Furthermore, to achieve the object of the present invention, the projection height L4 of each of the outer side surface and inner side surface (in other words, a substantially isosceles trapezoidal shape) of the pair of left and right hole formation projections 13a and 13b generally preferably falls within the range of 4.5 to 7.5 mm, more preferably, the range of 4.8 to 7.2 mm, and most preferably, the range of 5.0 to 7.0 mm, from the viewpoint of practicality. In addition, to achieve the object of the present invention, the area of each of the outer side surface and inner side surface (in other words, a substantially isosceles trapezoidal shape) of the pair of left and right hole formation projections 13a and 13b generally preferably falls within the range of 45 to 75 $mm^2$, more preferably, the range of 48 to 72 $mm^2$, and most preferably, the range of 50 to 70 $mm^2$, from the viewpoint of practicality. Note that the above-mentioned numerical value ranges of the length L3, projection height L4, and area substantially apply even when the shape of each of the pair of left and right hole formation projections 13a and 13b continuing to the pair of left and right end portions 11a and 11b of the outer peripheral portion 11 of the mask main body 6 is not a substantially isosceles trapezoidal shape but a substantially trapezoidal shape other than a substantially isosceles trapezoidal shape, a substantially rectangular shape, a substantially semi-circular shape, a substantially semi-elliptical shape, or a substantially semi-oval shape. Note also that the above-mentioned lower base means a portion (in other words, the proximal end or base) of the pair of left and right hole formation projections 13a and 13b, which continues to the pair of left and right end portions 11a and 11b.

Each of the string attaching short holes 15 to 18 shown in FIG. 1 has a short-hole shape, e.g., a substantially circular shape or a polygonal shape such as a substantially hexagonal shape or substantially octagonal shape, in a planar view. A diameter (in other words, a maximum length in a planar view) L5 (not shown) of each of the string attaching short holes 15 to 18 is substantially 2 mm. Accordingly, the area of each of the string attaching short holes 15 to 18 in a planar view is substantially 3.14 mm². A width L6 (not shown) of each of the bandage attaching long holes 22 and 23 in a planar view is substantially 1 mm. A length L7 (not shown) of each of the linearly extending bandage attaching long holes 22 and 23 in a planar view is substantially 10 mm. Also, substantially upper and lower end portions (in other words, the two end portions) of each of the bandage attaching long holes 22 and 23 have a substantially semi-circular shape in a planar view. Accordingly, the area of each of the bandage attaching long holes 22 and 23 in a planar view is substantially 9 mm² To achieve the object of the present invention, the diameter (in other words, the maximum length) L5 of each of the string attaching short holes 15 to 18 generally preferably falls within the range of 1.5 to 2.5 mm, more preferably, the range of 1.6 to 2.4 mm, and most preferably, the range of 1.7 to 2.3 mm, from the viewpoint of practicality. Also, to achieve the object of the present invention, the area of each of the string attaching short holes 15 to 18 in a planar view generally preferably falls within the range of 2.35 to 3.95 mm², more preferably, the range of 2.50 to 3.80 mm², and most preferably, the range of 2.62 to 3.66 mm², from the viewpoint of practicality. Furthermore, to achieve the object of the present invention, the width L6 of each of the string attaching long holes (in other words, the band attaching long holes) 22 and 23 in a planar view generally preferably falls within the range of 0.75 to 1.25 mm, more preferably, the range of 0.80 to 1.20 mm, and most preferably, the range of 0.82 to 1.18 mm, from the viewpoint of practicality. In addition, to achieve the object of the present invention, the length L7 of each of the string attaching long holes 22 and 23 in a planar view generally preferably falls within the range of 7.5 to 12.5 mm, more preferably, the range of 8.0 to 12.0 mm, and most preferably, the range of 8.2 to 11.8 mm, from the viewpoint of practicality. Also, to achieve the object of the present invention, the area of each of the bandage attaching long holes 22 and 23 in a planar view generally preferably falls within the range of 6.8 to 11.4 mm², more preferably, the range of 7.2 to 10.8 mm², and most preferably, the range of 7.5 to 10.5 mm², from the viewpoint of practicality.

As shown in FIGS. 1 and 2, a pair of left and right substantially triangular ventilation holes 25a and 25b for performing ventilation between the inside and outside of the mask main body 6 are formed in portions slightly above the left and right sides of the mask main body 6. Note that when the mask wearer 2 is wearing the mask main body 6, the pair of left and right ventilation holes 25a and 25b are arranged in positions corresponding to the left and right nostrils of the mask wearer 2 and portions around these nostrils. The right ventilation hole 25b has a shape which is substantially bisymmetrical to the shape of the left ventilation hole 25a. Also, a connector attaching portion 33 for attaching first and second connectors 31 and 32 is formed in a portion slightly below a substantially central portion of the mask main body 6. In addition, a hole 34 having a substantially pillar shape such as a substantially circular pillar shape is formed in the connector attaching portion 33. Furthermore, the connector attaching portion 33 is formed in the mask main body 6 so as to incline to the horizontal direction and vertical direction of the mask main body 6. This inclination direction of the connector attaching portion 33 can be a direction in which the connector attaching portion 33 projects outward from below.

2. Explanation of First to Fourth Connectors and Oxygen Supply Tube

As shown in FIGS. 1 and 2, the oxygen mask apparatus 1 includes the first connector 31, the second connector 32, a third connector 35, a gas supply tube 36, and a fourth connector (not shown). Note that each of the first to fourth connectors can integrally be molded from a substantially transparent (in other words, light-transmitting) hard synthetic resin such as hard vinyl chloride. Note also that the gas supply tube 36 can integrally be molded from a substantially transparent soft synthetic resin such as soft vinyl chloride. The first connector 31 includes a gas supply cylindrical portion 41 which substantially obliquely extends along substantially the axial direction of the first connector 31 and has a cylindrical shape such as a substantially circular cylindrical shape, and an upper-end surface portion 42 which is formed on the upper-end side of the cylindrical portion 41 so as to project toward the upper-end side, and has a pyramidal shape such as a substantially conical shape. Also, a substantially circular opening 43 for introducing a gas (for example, introducing oxygen to the inside of the mask main body 6) is formed in a substantially central portion of the substantially pyramidal upper-end surface portion 42. The first connector 31 is attached to the mask main body 6 by inserting the gas supply cylindrical portion 41 of the first connector 31 into the hole 34 from inside the mask main body 6.

As shown in FIGS. 1 and 2, a portion on the lower-end side of the second connector 32 forms a lower cylindrical portion 44 having a substantially cylindrical shape such as a substantially circular cylindrical shape to which the third connector 35 is attached. The lower cylindrical portion 44 normally extends in a substantially vertical direction. Also, a portion on the upper-end side of the second connector 32 is obliquely bent upward from the portion on the lower-end side of the second connector 32, so as to extend along substantially the axial direction of the first connector 31. An upper-end portion having a substantially cylindrical shape such as a substantially circular cylindrical shape of the second connector 32 is inserted between the gas supply cylindrical portion 41 of the first connector 31 and a cylindrical projecting wall of the mask main body 6. In addition, the third connector 35 includes a large-diameter, closed-end cylindrical portion 44 having a circular cylindrical shape or the like, and a small-diameter cylindrical portion 45 having a circular cylindrical shape or the like and connected to the lower end portion of the cylindrical portion 44 by integral molding or the like. Note that a through hole 46 for communicating with the small-diameter cylindrical portion 45 is formed in a substantially central position of the bottom of the large-diameter cylindrical portion 44. One end portion of the gas supply tube 36 is inserted into and connected to the small-diameter cylindrical portion 45. Also, the upper-end opening of the gas supply tube 36 communicates with the large-diameter cylindrical portion 44 through the through hole 46. Furthermore, the above-mentioned fourth connector (not shown) is connected to the other end portion of the gas supply tube 36. The fourth connector can be connected to a gas cylinder (not shown) such as an oxygen cylinder or to a gas supply nozzle (not shown) installed in a hospital room or the like as needed. Accordingly, regardless of whether or not the oxygen mask apparatus 1 is put on the face 3 of the mask wearer 2 as shown in FIGS. 1 and 2, a gas flow can be supplied from the gas introduction opening 43 of the first connector 31 to a space (in other words, a gas introduction space existing between the face 3 and mask main body 6) 47 in the mask main body 6.

3. Explanation of Operation of Putting Oxygen Mask Apparatus on Mask Wearer

Each of the first and second head-worn rubber strings (in other words, the flat and relatively narrow elastic members) 14 and 21 to be used to put the oxygen mask apparatus 1 on the mask wearer 2 is formed into a tape shape having a relatively small width, and may be a fabric woven by a cotton thread and a polyurethane fiber thread (particularly, a polyurethane elastic fiber thread). Each of two end portions 51 of the head-worn rubber strings 14 and 21 is covered with a tube 52 having a substantially cylindrical shape such as a substantially circular cylindrical shape, thereby being molded into a substantially pillar shape such as a substantially circular pillar shape. Note that the tube 52 can be made from a heat-contractive synthetic resin. Note that the diameter (in other words, the maximum length of the cross section) of the outer circumferential surface of each tube 52 is substantially 2 mm. Accordingly, the cross-sectional area of an attaching target portion 54 including the tube 52 and the end portion 51 of the head-worn rubber strings 14 and 21 surrounded by the outer circumferential surface of the tube 52 is substantially 3.14 mm$^2$ The thickness of the cross section of a middle portion 53 of each of the head-worn rubber strings 14 and 21 except for the two end portions 51 is substantially 1.5 mm. Also, the length of the cross section of the middle portion 53 is substantially 6 mm. To achieve the object of the present invention, the diameter (in other words, the above-mentioned maximum length) of each of the outer circumferential surfaces of the two end portions 51 of the tube 52 generally preferably falls within the range of 1.5 to 2.5 mm, more preferably, the range of 1.6 to 2.4 mm, and most preferably, 1.7 to 2.3 mm, from the viewpoint of practicality. In addition, to achieve the object of the present invention, the cross-sectional area of the attaching target portion 54 generally preferably falls within the range of 2.36 to 3.94 mm$^2$, more preferably, the range of 2.50 to 3.78 mm$^2$, and most preferably, the range of 2.62 to 3.66 mm$^2$, from the viewpoint of practicality. Furthermore, to achieve the object of the present invention, the thickness of the cross section of the middle portion 53 of each of the head-worn rubber strings (in other words, the flat and relatively narrow head-worn elastic members) 14 and 21 except for the two end portions 51 generally preferably falls within the range of 1.12 to 1.88 mm, more preferably, the range of 1.20 to 1.80 mm, and most preferably, the range of 1.25 to 1.75 mm, from the viewpoint of practicality. Also, to achieve the object of the present invention, the length of the cross section of the middle portion 53 generally preferably falls within the range of 4.5 to 7.5 mm, more preferably, the range of 4.8 to 7.2 mm, and most preferably, the range of 5.0 to 7.0 mm, from the viewpoint of practicality.

Each of the head-worn elastic bandage 24 and the second head-worn elastic bandage (in other words, the flat and relatively wide head-worn elastic members) to be used to put the oxygen mask apparatus 1 on the mask wearer 2 is formed into a tape shape having a relatively large width, and is a fabric woven by a cotton thread and a polyurethane fiber thread (particularly, a polyurethane elastic fiber thread). Note that the thickness of the cross section of each of the head-worn elastic bandage 24 and the above-mentioned second head-worn elastic bandage is substantially 0.5 mm. Note also that the length of the cross section of each of the head-worn elastic bandage 24 and the above-mentioned second head-worn elastic bandage is substantially 38 mm. To achieve the object of the present invention, the thickness of the cross section of each of the head-worn elastic bandage 24 and the above-mentioned second head-worn elastic bandage generally preferably falls within the range of 0.38 to 0.62 mm, more preferably, the range of 0.40 to 0.60 mm, and most preferably, the range of 0.42 to 0.58 mm, from the viewpoint of practicality. Also, to achieve the object of the present invention, the length of the cross section of each of the head-worn elastic bandage 24 and the above-mentioned second head-worn elastic bandage generally preferably falls within the range of 28.5 to 47.5 mm, more preferably, the range of 30.5 to 45.6 mm, and most preferably, the range of 31.6 to 44.4 mm, from the viewpoint of practicality.

When attaching the head-worn rubber string 14 or 21 to the string attaching short holes 15 to 18 of the left and right end portions 11a and 11b of the mask main body 6, one of the left and right string attaching short holes 15 to 18 shown in FIGS. 1 and 2 is first selected as an attaching portion target. In this case, the left and right hole formation projections 13a and 13b show that they are attaching portions at a standard height of the left and right end portions 11a and 11b of the mask main body 6. When attaching the head-worn rubber string 14 or 21 to the attaching portions at the standard height, therefore, the mask wearer 2 or the like needs only to attach the head-worn rubber string 14 or 21 to the hole formation projections 13a and 13b. Note that the left and right hole formation projections 13a and 13b show that they are the attaching portions at the standard height of the left and right end portions 11a and 11b of the mask main body 6 as described above, so the mask wearer 2 or another can relatively easily and relatively simply perform the operation of putting the mask main body 6 on the head 26 of the mask wearer 2.

Next, an attaching operation of attaching, e.g., the second head-worn rubber string 21 of the first and second head-worn rubber strings 14 and 21 to, e.g., the string attaching short holes 17 of the string attaching short holes 15 to 18 of the right end portion 11b of the mask main body 6 will be explained with reference to FIGS. 3 and 4. Note that an attaching operation of attaching the second head-worn rubber string 21 to the string attaching hole 17 of the left end portion 11a of the mask main body 6, an attaching operation of attaching the second head-worn rubber string 21 to one of the string attaching short holes 15, 16, and 18 of the left end portion 11a or right end portion 11b, and an attaching operation of attaching the first head-worn rubber string 14 to one of the string attaching short holes 15 to 18 of the left end portion 11a or right end portion 11b are substantially the same as the attaching operation to be explained below.

Figure 3:
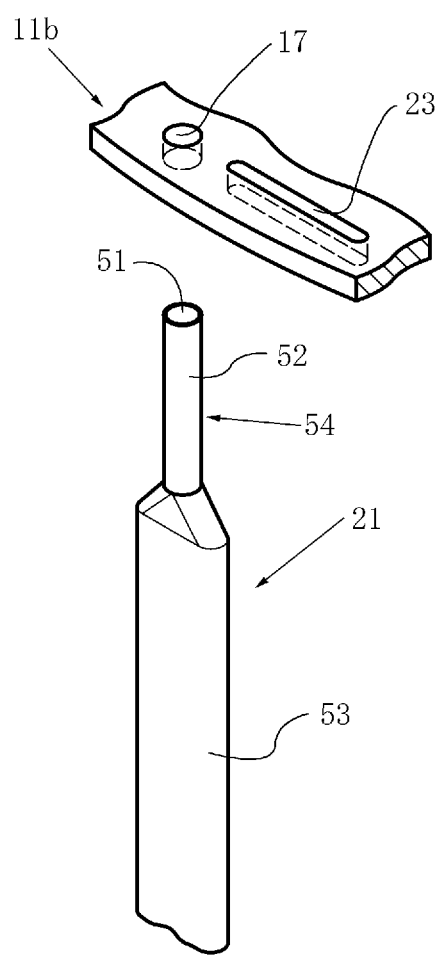
FIG. 3 is a perspective view of main parts showing the initial stage of an operation of attaching a head-worn rubber string to a string attaching short hole in the oxygen mask apparatus in the first wearing state shown in FIG. 2.
Figure 4:
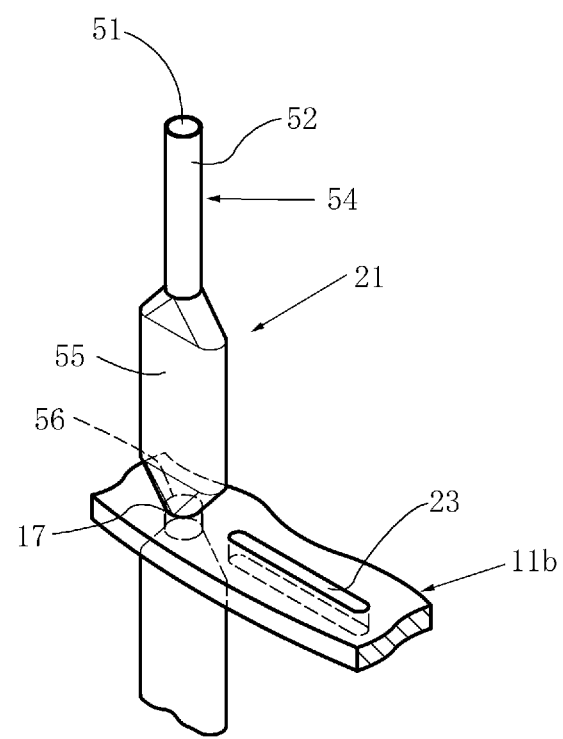
FIG. 4 is a perspective view of main parts showing the completion stage of the operation of attaching the head-worn rubber string (in other words, a head-worn India rubber string) to the string attaching short hole in the oxygen mask apparatus in the first wearing state shown in FIG. 2.

As shown in FIG. 3, when attaching the second head-worn rubber string 21 to the string attaching hole 17 of the right end portion 11b of the mask main body 6, one of the tubes 52 of the longitudinal second head-worn rubber string 21 is made to pass through the string attaching short hole 17 of the right end portion 11b of the mask main body 6 by inserting the tube 52 from the original lower side surface of the string attaching short hole 17. Then, the distal end portion of the tube 52 made to pass through the string attaching short hole 17 is pulled out from the right end portion 11b from the original upper side surface of the right end portion 11b. Consequently, as shown in FIG. 4, the tube 52 and a portion 55 on the distal end side of the middle portion 53, which continues to the tube 52, pass through the string attaching short hole 17. In this case, a portion of the middle portion 53, which continues to the portion 55 on the distal end side, is supported as a constricted portion 56 in the string attaching short hole 17 by the outer circumferential portion of the string attaching short hole 17 of the right end portion 11b. Note that the second head-worn rubber string 21 is formed as an elastic member as described previously. Accordingly, there is substantially no possibility that when putting the mask main body 6 on the head 26 or when the mask main body 6 is already put on the head 26, the second head-worn rubber string 21 is removed from the string attaching short hole 15 by the force applied to the second head-worn rubber string 21. Note that when removing the second head-worn rubber string 21 from the string attaching short hole 17, the operation is reverse to the above-described attaching operation, i.e., the second head-worn rubber string 21 need only be pulled out from the string attaching short hole 17.

Figure 5:
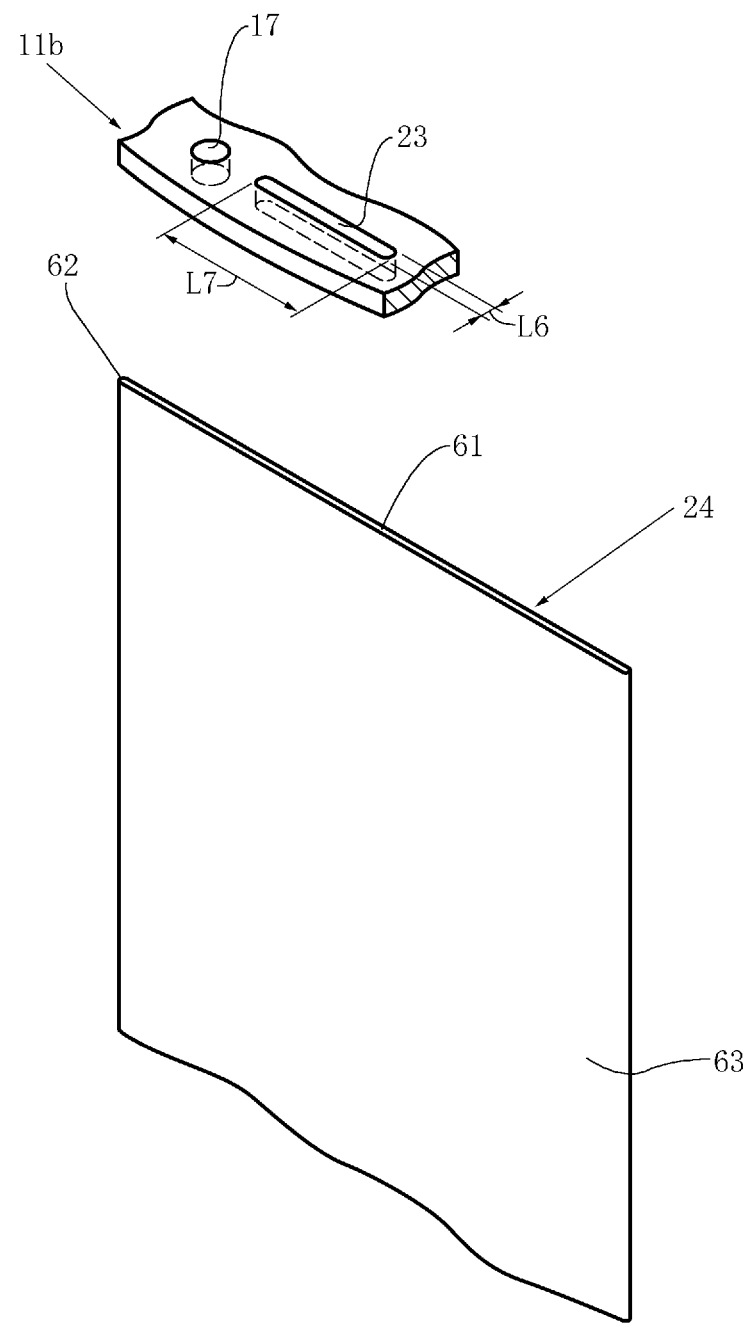
FIG. 5 is a perspective view of main parts showing the initial stage of an operation of attaching a head-worn elastic bandage to a bandage attaching long hole in a second wearing state of the oxygen mask apparatus shown in FIG. 1.

An attaching operation of attaching, for example, the head-worn elastic bandage 24 of the head-worn elastic bandage 24 and the above-mentioned second head-worn elastic bandage to, e.g., the bandage attaching long hole 23 of the bandage attaching long holes 22 and 23 of the right end portion 11b of the mask main body 6 will be explained below with reference to FIGS. 5 to 7. Note that an attaching operation of attaching the head-worn elastic bandage 24 to the bandage attaching long hole 23 of the left end portion 11a of the mask main body 6, an attaching operation of attaching the head-worn elastic bandage 24 to the bandage attaching long holes 22 of the left end portion 11a or right end portion 11b of the mask main body 6, and an attaching operation of attaching the above-mentioned second head-worn elastic bandage to one of the bandage attaching long holes 22 and 23 of the left end portion 11a or right end portion 11b are substantially the same as the attaching operation to be explained below.

Figure 6:
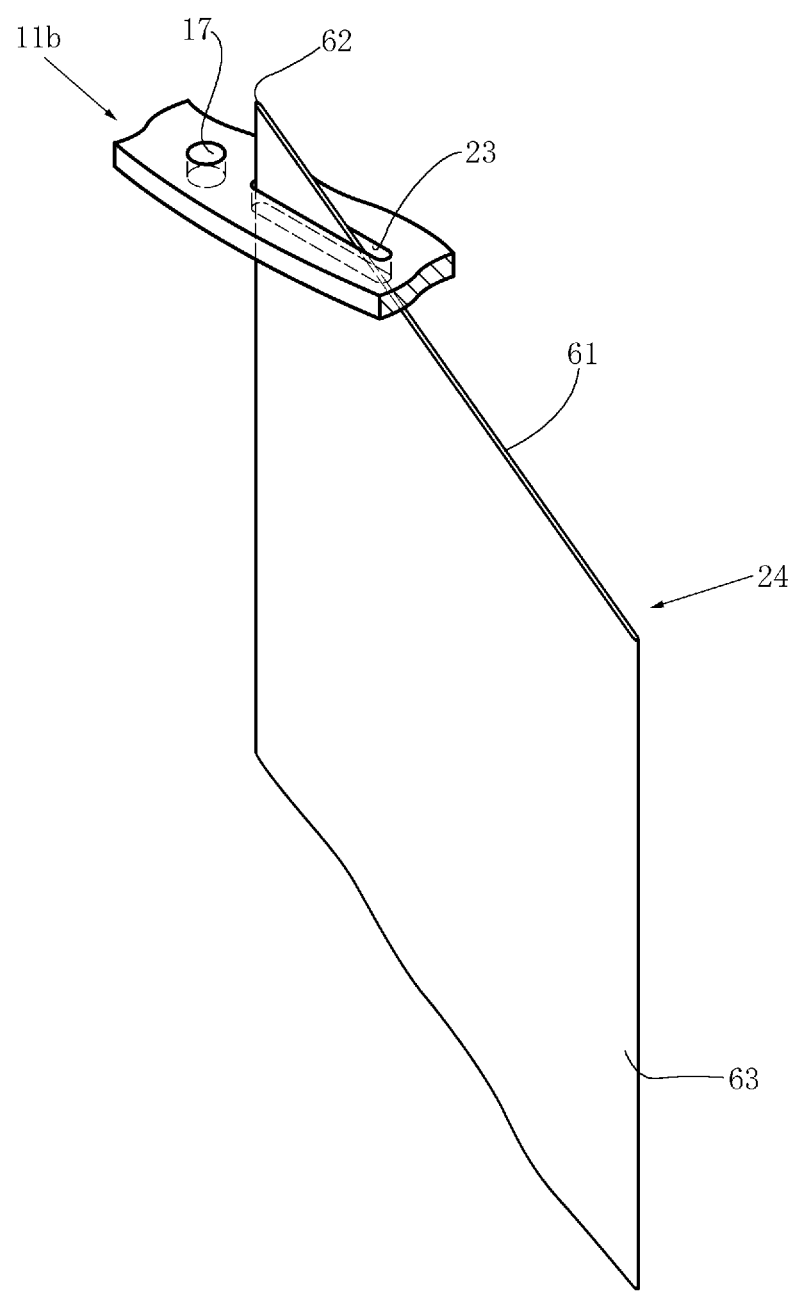
FIG. 6 is a perspective view of main parts showing the middle stage of the operation of attaching the head-worn elastic bandage to the bandage attaching long hole in the second wearing state of the oxygen mask apparatus shown in FIG. 1.
Figure 7:
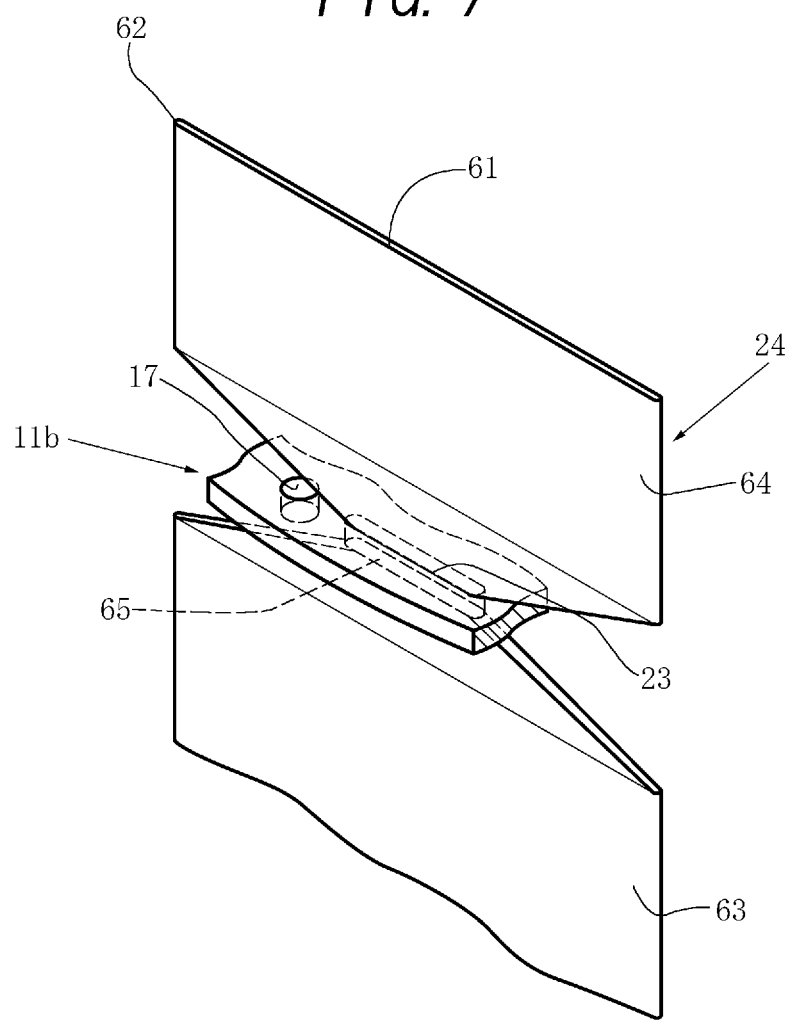
FIG. 7 is a perspective view of main parts showing the completion stage of the operation of attaching the head-worn elastic bandage to the bandage attaching long hole in the second wearing state of the oxygen mask apparatus shown in FIG. 1.

When attaching the head-worn elastic bandage 24 to the bandage attaching long hole 23 of the right end portion 11b of the mask main body 6, one of corners 62 of one of end portions 61 of the longitudinal head-worn elastic bandage 24 shown in FIG. 6 is made to pass through the bandage attaching long hole 23 of the right end portion 11b of the mask main body 6 from the original lower side surface of the bandage attaching long hole 23. Then, the corner 62 passed through the bandage attaching long hole 23 is pulled out against the right end portion 11b from the original upper side surface of the right end portion 11b. Consequently, as shown in FIG. 7, the corner 62, and a portion 64 on the distal end side of a middle portion 63 of the longitudinal head-worn elastic bandage 24, which continues to the corner 62, are made to pass through the bandage attaching long hole 23. In this case, a portion of the middle portion 63, which continues to the portion 64 on the distal end side, is supported as a constricted portion 65 in the bandage attaching long hole 23 by the outer circumferential portion of the bandage attaching long hole 23 of the right end portion 11b. Note that the head-worn elastic bandage 24 is formed as an elastic member as described previously. Accordingly, there is substantially no possibility that when putting the mask main body 6 on the head 26 or when the mask main body 6 is already put on the head 26, the head-worn elastic bandage 24 is removed from the bandage attaching long hole 23 by the force applied to the head-worn elastic bandage 24. Note that when removing the head-worn elastic bandage 24 from the bandage attaching long hole 23, the operation is reverse to the above-described attaching operation, i.e., the head-worn elastic bandage 24 need only be pulled out from the bandage attaching long hole 23.

Having described a specific preferred embodiment of the present invention with reference to the accompanying drawings, it is to be understood that the invention is not limited to these precise embodiment, and that various changes and modifications may be effected therein by one skilled in the art without departing from the scope or spirit of the invention as defined in the appended claims.

For example, in the above-described embodiment, the pair of upper and lower bandage attaching long holes 22 and 23 extending along the pair of left and right end portions 11a and 11b are formed into a substantially linear shape. However, the pair of upper and lower bandage attaching long holes 22 and 23 need not have a substantially linear shape, and may also have, e.g., a shape which is slightly curved along the pair of left and right end portions 11a and 11b.

Also, in the above-described embodiment, no bandage attaching long holes are formed in portions above the pair of left and right bandage attaching long holes 22. In portions above the pair of left and right bandage attaching long holes 22, however, it is also possible to form a pair of left and right third bandage attaching long holes in the left end portion 11a and right end portion 11b of the outer peripheral portion 11.

In addition, in the above-described embodiment, the pair of left and right string attaching short holes 15 are formed in the pair of left and right hole formation projections 13a and 13b, and the pair of left and right bandage attaching long holes 22 are formed in the pair of left and right end portions 11a and 11b so that the pair of left and right bandage attaching long holes 22 are formed adjacent to and substantially oppose the pair of left and right string attaching short holes 15. However, it is also possible to form the pair of left and right bandage attaching long holes 22 in the pair of left and right hole formation projections 13a and 13b, and form the pair of left and right string attaching short holes 15 in the pair of left and right end portions 11a and 11b so that the pair of left and right string attaching short holes 15 are formed adjacent to and substantially oppose the pair of left and right bandage attaching long holes 22. Note that from the viewpoint of the strength of the pair of left and right hole formation projections 13a and 13b, the above-described embodiment (i.e., the former) is superior to the latter.

Furthermore, in the above-described embodiment, the two end portions of each of the first and second head-worn rubber strings 14 and 21 are attached to one pair of the left and right string attaching short holes 15 to 18. However, the head-worn rubber strings 14 and 21 may also be attached to ears 66 of the mask wearer 2 by an ear strap method. In this case, each of the first and second head-worn rubber strings 14 and 21 is formed by left and right rubber strings, and the middle portion of each of the left and right rubber strings has an ear strap portion having a substantially loop shape. The end portions of each of the left and right rubber strings are attached to two of the left or right string attaching short holes 15 to 18, thereby attaching the middle portion of each of the left and right rubber strings to the ear 66 by the ear strap method.

The invention claimed is:

1. A gas supply mask apparatus comprising a mask main body wearable on a head of a mask wearer and configured to allow for introduction of a gas into a gas introduction space existing between the mask main body and the face of the mask wearer when the apparatus is placed on the head of the wearer,
wherein a string attaching short hole and a band attaching long hole are formed in each of a left end portion and a right end portion of an outer peripheral portion of the mask main body, wherein a left hole formation projection is formed in a substantially middle portion of the left end portion and a right hole formation projection is formed in a substantially middle portion of the right end portion, such that the left hole formation projection and the right hole formation projection project substantially outward to left and right, respectively; and the string attaching short hole is formed in each of the hole formation projections and the band attaching long holes are formed in the outer peripheral portion with each band attaching long hole adjacent to a hole formation projection, or the band attaching long hole is formed in each of the hole formation projections and the string attaching short holes are formed in the outer peripheral portion with each string attaching short hole adjacent to a hole formation projection.

2. The apparatus of claim 1, wherein the left end and right end portions of the outer peripheral portion are formed into a substantially flat surface.

3. The apparatus of claim 1, wherein the left hole formation projection and the right hole formation projection are each respectively integrated with and substantially flush with the left end portion and the right end portion.

4. The apparatus of claim 1, wherein the left and right hole formation projections are each individually formed into a substantially trapezoidal shape, a substantially rectangular shape, a substantially semi-circular shape, a substantially semi-elliptical shape, or a substantially semi-oval shape.

5. The apparatus of claim 4, wherein the left and right hole formation projections are each formed into a substantially isosceles trapezoidal shape which narrows substantially as it projects to the left or right.

6. The apparatus of claim 4, wherein each of the left and right hole formation projections independently has: a base having a length of 10.5 to 17.5 mm, a projection height of 4.5 to 7.5 mm, and an area of 45 to 75 mm$^2$.

7. The apparatus of claim 4, wherein each of the left and right hole formation projections independently has: a base having a length of 11.2 to 16.8 mm, a projection height of 4.8 to 7.2 mm, and an area of 48 to 72 mm$^2$.

8. The apparatus of claim 4, wherein each of the left and right hole formation projections independently has: a base having a length falling 11.7 to 16.3 mm, a projection height of 5.0 to 7.0 mm, and an area of 50 to 70 mm$^2$.

9. The apparatus of claim 1, wherein the ratio of the vertical length from the upper end of the mask main body to a substantially center point between the left and right hole formation projections to the vertical length of the mask main body falls within a range of 0.38 to 0.48.

10. The apparatus of claim 9, wherein the ratio falls within a range of 0.39 to 0.47.

11. The apparatus of claim 9, wherein the ratio falls within a range of 0.40 to 0.46.

12. The apparatus of claim 1, wherein each of the string attaching short holes, in a planar view, has a maximum length of 1.5 to 2.5 mm and an area of 2.35 to 3.95 mm$^2$.

13. The apparatus of claim 1, wherein each of the string attaching short holes, in a planar view, has a maximum length of 1.6 to 2.4 mm and an area of 2.50 to 3.80 mm$^2$.

14. The apparatus of claim 1, wherein each of the string attaching short holes, in a planar view, has a maximum length of 1.7 to 2.3 mm and an area of 2.62 to 3.66 mm$^2$.

15. The apparatus of claim 1, wherein each of the band attaching long holes, in a planar view, has a width of 0.75 to 1.25 mm, a maximum length of 7.5 to 12.5 mm, and an area of 6.8 to 11.4 mm$^2$.

16. The apparatus of claim 1, wherein each of the band attaching long holes, in a planar view, has a width of 0.80 to 1.20 mm, a maximum length of 8.0 to 12.0 mm, and an area of 7.2 to 10.8 mm$^2$.

17. The apparatus of claim 1, wherein each of the band attaching long holes, in a planar view, has a width of 0.82 to 1.18 mm, a maximum length of 8.2 to 11.8 mm, and an area of 7.5 to 10.5 mm$^2$.

18. The apparatus of claim 1, wherein the string attaching short holes are circular.

19. The apparatus of claim 1, wherein the band attaching long holes have a substantially linear shape.

20. The apparatus of claim 1, comprising four string attaching short holes wherein two string attaching short holes are formed along a substantially vertical direction in each of the left and right end portions.

21. The apparatus of claim 1, comprising four band attaching long holes wherein two band attaching long holes extend linearly along each of the left and right end portions.

22. The apparatus of claim 1, wherein the outer peripheral portion further comprises upper end and lower end portions which connect the left end and right end portions.

23. A gas supply mask apparatus comprising a mask main body wearable on a head of a mask wearer and configured to allow for introduction of a gas into a gas introduction space existing between the mask main body and the face of the mask wearer when the apparatus is placed on the head of the wearer, the apparatus further comprising four short circular string attaching holes wherein two of the short circular string attaching holes are formed along a substantially vertical direction in each of left and right end portions of an outer peripheral portion of the mask main body; and four long band attaching substantially linear holes wherein two of the long band attaching substantially linear holes extend linearly along each of the left and right end portions.

* * * * *